United States Patent [19]
Lovett et al.

[11] Patent Number: 4,585,739
[45] Date of Patent: Apr. 29, 1986

[54] PLASMID FOR FOREIGN GENE EXPRESSION IN B. SUBTILIS

[75] Inventors: Paul S. Lovett, Columbia, Md.; Ronald G. Schoner, Zionsville, Ind.

[73] Assignee: E. I. Du Pont de Nemours and Company, Wilmington, Del.

[21] Appl. No.: 472,641

[22] Filed: Mar. 7, 1983

[51] Int. Cl.[4] .................. C12N 1/20; C12N 1/00; C12N 15/00

[52] U.S. Cl. ................... 435/253; 435/317; 435/172.3; 935/29; 935/38; 935/60

[58] Field of Search ........... 435/172, 253, 317, 172.3; 935/29, 38

[56] References Cited

FOREIGN PATENT DOCUMENTS 36259 9/1981 European Pat. Off. .
63494 10/1982 European Pat. Off. .
2090600 7/1982 United Kingdom .

OTHER PUBLICATIONS

Wallace et al., Science, vol. 209, pp. 1396–1400, Sep. 19, 1980.
Smith et al., Genetic Engineering, Principles and Methods, vol. 3, edited by Setlow et al., Plenum Press, pp. 1–32 (1981).
Lovett et al., J. Bacteriol. 127, 817–828 (1976).
Ehrlich, Proc. Natl. Acad. Sci. USA 74, 1680–1682 (1977).
Keggins et al., Proc. Natl. Acad. Sci. USA 75, 1423–1427.
Gryczan et al., Proc. Natl. Acad. Sci. USA 75, 1428–1432 (1978).
Goldbard et al., Nature 293, 309–311 (1981).
Williams et al., Gene 16, 199–206 (1981).

*Primary Examiner*—Alvin E. Tanenholtz
*Attorney, Agent, or Firm*—Frederick D. Hunter

[57] ABSTRACT

The invention provides a mutant plasmid useful for introducing into *B. subtilis* foreign DNA, the nucleic acid sequence of which codes for production of a desired product. The plasmid is constructed from (1) a segment of *B. pumllus* DNA containing a chloramphenicol acetyltransferase gene plus an EcoRI* promoter fragment cloned from phage SPO2 DNA and a (2) portion of a *B. subtilis* plasmid, pUB110. The plasmid gives enhanced expression of genes coding for certain products, such as dihydrofolate reductase.

11 Claims, 4 Drawing Figures

FIG. 1

```
5'
     1              10                 20                 30       "-35A"    40
     G A A T T C A C A C T G G C C T T G G T T A A G G T T A A G A T G T G G A C G G
       Eco RI              HaeIII

+2             0       0                         +2
     41            50                60       "-10A"    70                  80
     A A T G G G T A A A G T G T A G T A A A G T A C A A T T A A T C G G G A G C T T
                                                                              DdeI

+2                                         +2
     81            90                100                 110 "RBS"           120
     A G A T G T C C C T T C A A C A T C T T A T A T A G A A G G G A A G G T T G G C

+2                +2                          +1
     121           130 "-35B"      140                150       "-10B"    160
     A A A T G G A A·A T T·G A A·A G A·A T T·A A C·G A G·C A T·A C A G T A·A A A·T T

+2                  +2
     161           170                180                190       "-35C"    200
     T·T A T·A T G·T C T·T A C·G G A·G A T·A T T·G A·A G A T·C G C·G G T·T T T·G A C·
                                                         Sau 3AI

+2            +2                 +2
     201           210      "-10C" 220               230                     240
     A G A·G A A·G A A·A T T·T G G·T A T·A A C·C G T·G A G·C G C·A G T·G A A·G A A·C

+2                +2
     241           250                260                270                 280
     T T·T T C·T G G·G A A·G T C·A T G·G A T·G A A·G T T·C A T·G A A·G A A·G A G·G A 0
     281           290                300                310                  320
     A·T T C·A C A·T C A·A T G·C G A·T G T·C C C·A G A·G A A·T A T·T G G·T A T·A A·
     Eco RI

+1
     321           330                340          (A)  350                  +1
                                                                             360
     G A T·A T T·A T G·A A G·C A T·T T C·G A A·A A A·A G·A A C·A T A·T A C·A T G·A

0            +1       +1         0      0    +1
     361           370                380                390                 400
     G C·C A A·T A A·C A A·A T G·A A A·A T G·A G T·T A G·T G A·A T G·A A T·G T C·A T

+1  +1        0                                                         0
     401           410                420                430                 440
     A·A T A·G A A·T G A·A T A·C C T·C A G·C G G·A G A·A A A·C A T A·T A·T A G·C A C·

0                             0
     441           450                460                470                 480
     T A G·A A A·A T T·C A C·G T T·G G·G C A·A G A·T G A·C T T·A C G·A A G·A G T·T

481
     G C·T G C·A G
       Pst I
                 3'
```

A — Tn9 CAT
B — CAT FROM pPL 608
C — pBR 322 FRAGMENT
D — IFN
E — pUB 110
F — SpO2 PROMOTER

PLASMID FOR FOREIGN GENE EXPRESSION IN B. SUBTILIS

BACKGROUND OF THE INVENTION

This invention relates to a hybrid plasmid and, in particular, a hybrid plasmid useful for expressing foreign genes in *B. subtilis*. Considerable interest exists in the application of genetic engineering techniques for the production of commercially valuable products such as insulin, human and animal growth hormones and enzymes. Much of the work to date has involved use of *Escherichia coli* as the host into which foreign genetic material is introduced. Expression of the genetic material in *E. coli* results in production of desired products. When combined with growth of genetically engineered cells in culture, it permits production of the desired products in commercially meaningful yields. Unfortunately, use of *E. coli* as a host is associated with certain disadvantages. As a result, alternative hosts, including other bacteria and yeast, are under investigation.

One particularly promising host for commercial applications of genetic engineering is *Bacillus subtilis*. *B. subtilis* is a nonpathogenic, gram-positive bacterium which is eaten daily by millions of Japanese as part of a fermented soybean product. *B. subtilis* may be the safest bacterium in which to achieve expression of foreign genes whose products, e.g. interferon, will be purified and subsequently injected into humans for at least two reasons. First, *B. subtilis* is known to be nonpathogenic. Secondly, *E. coli* is known to produce endotoxins which may contaminate genetic products and induce endotoxic shock in humans.

*Bacillus subtilis* is a prokaryote that has been used for gene cloning. Phenotypic expression of foreign genes in *B. subtilis* has been until recently obtained only with genes originating in gram-positive species such as *Bacillus staphylococcus* and *Streptococcus*, see for example Lovett et al., J. Bacteriol. 127, 817–828 (1976); Ehrlich, Proc. Natl. Acad. Sci. 74, 1680–1682 (1977); Keggins et al., Proc. Natl. Acad. Sci. 75, 1423–1427 (1978); and Gryczan et al., Proc. Natl. Acad. Sci. 75, 1428–1432 (1978). Goldfarb et al., Nature 293, 309–311, (1981) disclose the expression in *B. subtilis* of *E. coli* chloramphenicol resistance by supplanting the native regulatory element(s) of the gene coding for this activity with *B. subtilis* DNA fragments.

European Patent Application No. 81300858.8, Publication No. 0,036,259, discloses a method and a cloning vector for the controlled accumulation of cloned heterologous gene products in *Bacillus subtilis*. The cloning vector is capable of being replicated in *B. subtilis* and includes the heterologous gene located and oriented such as to be under the control of an operator, promoter and ribosomal binding site sequence. The gene codes for a protein which is under the control of a transport mechanism by which the protein is secreted by the *B. subtilis*.

European Patent Application No. 82302027.6, published on Oct. 27, 1982 as Publication No. 0,063,494, discloses a method and cloning vectors useful for the production of cloned heterologous gene products in *B. subtilis*. Use of the method and vectors allows the host to produce the heterologous gene product as a single unfused peptide having no extraneous amino acids attached that will accumulate within transformed host organisms. The publication specifically discloses the use of a beta-lactamase promoter to express human fibroblast ($\beta$) interferon in *B. subtilis*.

Williams et al., Gene 16, 199–206 (1981) disclose a plasmid pPL608 which can be used to express the mouse dihydrofolate reductase (DHFR) gene and a segment of the *E. coli* trp operon in *B. subtilis*. The cloned mouse gene confers trimethoprim resistance on *B. subtilis*. The mouse gene was inserted at a PstI site preceding a chloroamphenicol acetyltransferase (CAT) gene present on pPL608 and its expression is not chloramphenicol inducible. The pPL608 plasmid has a mass of about 3.3 Md and consists of a major portion of pUB110 joining to a 0.8 Md segment of *B. pumilus* DNA containing a CAT gene plus a 0.2 Md EcoRI* promoter fragment cloned from phage SPO2 DNA.

Copending U.S. patent application Ser. No. 307,604, filed Oct. 1, 1981 (now abandoned) and designating P. S. Lovett as inventor, discloses a plasmid useful for introducing into *B. subtilis* foreign DNA, the nucleic acid sequence of which codes for the production of a desired product, comprising a double-stranded DNA molecule which includes a promoter DNA sequence which is not derived from *B. subtilis* plasmid DNA and a DNA sequence derived from a *B. subtilis* plasmid. The application discloses that the foreign DNA can include a gene coding for the production of a polypeptide product such as insulin, α-thymosin, growth hormones, enzymes, antibodies and the various interferons. The application further discloses that preferably the promoter is obtained from SPO2 and the *B. subtilis* plasmid source is *B. subtilis* plasmid pUB110.

SUMMARY OF THE INVENTION

The present invention provides a plasmid useful for introducing into *B. subtilis* foreign DNA, the nucleic acid sequence of which codes for production of a desired product. The plasmid comprises (1) a double-stranded DNA segment of *B. pumilus* strain NCIB8600 DNA containing a chloramphenicol acetyltransferase gene plus an EcoRI* promoter fragment cloned from phage SPO2 DNA and (2) a portion of a *B. subtilis* plasmid pUB110. The plasmid has a mutation in its EcoRI to PstI fragment downstream from the promoter fragment wherein an additional adenosine nucleotide is present. The nucleotide sequence for the EcoRI to PstI fragment is given in FIG. 1 of the drawing.

BRIEF DESCRIPTION OF THE DRAWING

FIG. 1 is the nucleotide sequence for the promoter fragment and the EcoRI to PstI fragment of the plasmid of the invention.

DETAILED DESCRIPTION OF THE INVENTION

Figure 2:
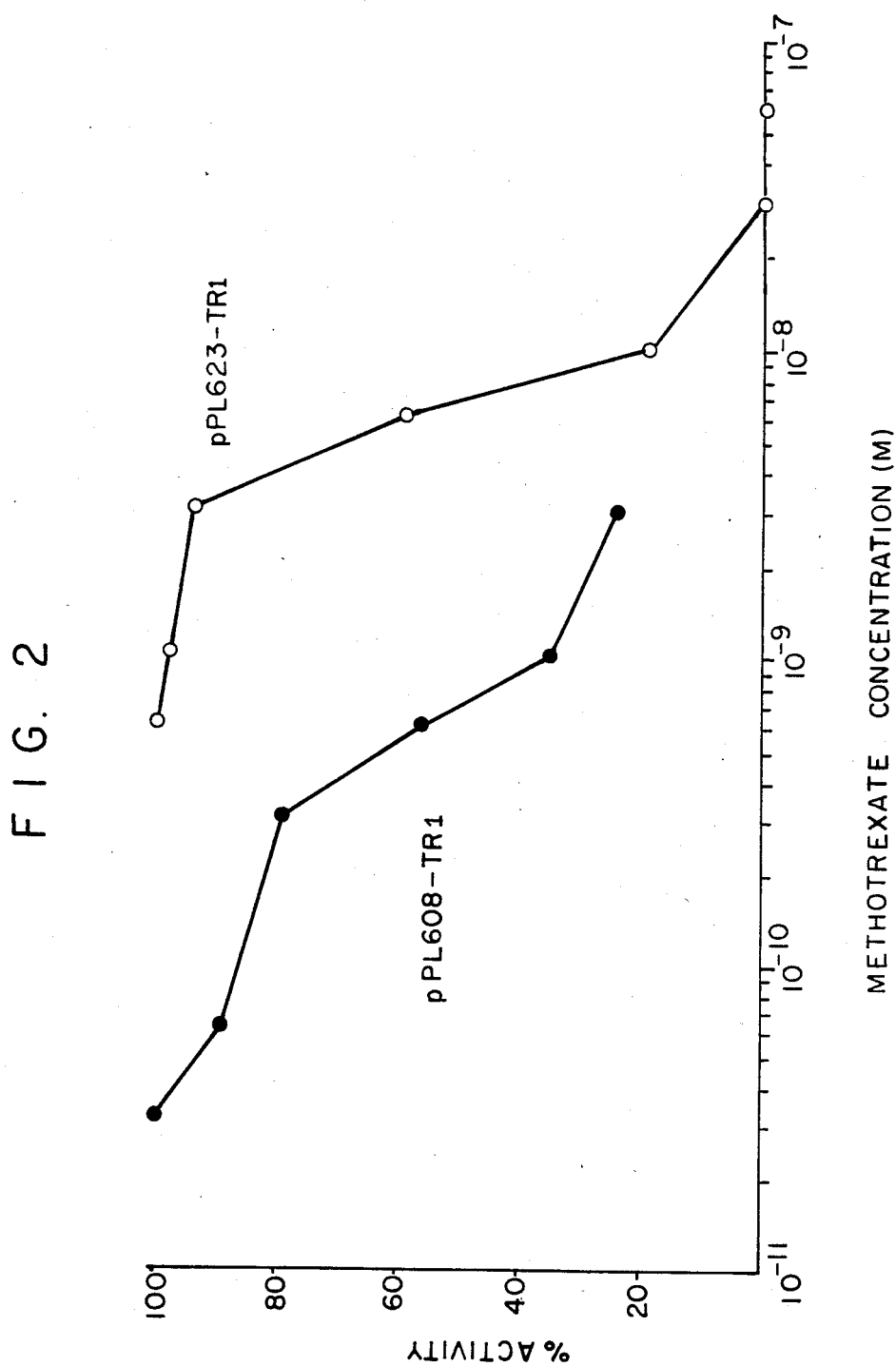
FIG. 2 is a graph of methotrexate reduction of DHFR activity.

A plasmid has been created which is useful for the introduction into *Bacillus subtilis* of foreign DNA whose nucleic acid sequence includes one or more genes which code for production of desired products. Preferably, the foreign DNA is a mouse gene coding for dihydrofolate reductase (DHFR) or a gene coding for the production of human interferon. More preferably the foreign DNA codes for production of human interferon and, most preferably, it codes for production $\beta$-interferon. When the foreign DNA is a mouse gene coding for production of dihydrofolate reductase enhanced expression is obtained with transformed *B. subtilis* strain BGSCIS53.

The plasmid of the invention comprises (1) a double-stranded DNA segment of *B. pumilus* DNA containing a chloramphenicol acetyltransferase gene plus an EcoRI* promoter fragment cloned from phage SPO2 DNA and (2) a portion of a *B. subtilis* plasmid pUB110. The plasmid differs from a known plasmid of this description, pPL608, in that the plasmid of the invention has a mutation in its EcoRI to PstI fragment downstream from the promoter fragment. The segment of *B. pumilus* DNA is obtained from *B. pumilus* strain NCIB8600. Preferably, the *B. subtilis* used for transformation is strain BGSCIS53. *B. subtilis* strain BGSCIS53, transformed with plasmids of the invention, has been deposited with the American Type Culture Collection (ATCC), Rockville, Md. and bears deposit accession numbers ATCC 39292, 39293 and 39294. These deposits are available to the public upon the grant of a patent to the assignee. However, it should be understood that the availability of a deposit does not constitute a license to practice the subject invention in derogation of patent rights granted by governmental action.

The plasmid of the invention is obtained by mutation of plasmid pPL608-TR1. Plasmid pPL608-TR1 contains a 1.5 kb DNA fragment harboring the mouse DHFR gene inserted in the PstI site of plasmid pPL608. The source of the mouse DHFR gene was pDHFR11. Plasmid pPL608 has a mass of about 3.3 Md and consists of a major portion of plasmid pUB110 joined to a 0.8 Md segment of *B. pumilus* DNA containing a CAT gene, plus a 0.2 Md, 0.3 kb, EcoRI* promoter fragment cloned from phage SPO2 DNA. Plasmid pPL608 is derived from plasmid pPL603. Plasmids pPL603, pPL608 and pPL608-TR1 have been described previously by Williams et al., J. Bacteriol. 146, 1162–1165 (1981); and Williams et al., Gene 16, 199–206 (1981). The disclosures of these publications are incorporated herein by reference.

Methods for identifying, recovering and purifying the various DNA segments which are portions of the plasmid of the invention are known to those skilled in the art as are methods for ligating the segments, transforming bacterial cells, cloning and recovering products synthesized. Accordingly, the methods will only be described by reference to specific embodiments of the invention set forth hereinafter. Preparation of the mutant plasmid of the invention is next discussed.

Plasmid pPL608-TR1 is prepared according to procedures given in Williams et al., Gene 16, 199–206 (1981). Briefly, plasmids pDHFR11 (1 μg/ml) and pPL608 (1 μg/ml) were digested with PstI, annealed, ligated, and transformed into *B. subtilis* strain BGSCIS53. Neomycin-resistant transformants were selected and each was transferred to appropriately supplemented MinCH containing 25 μg/ml of trimethoprim (MinCH-TP). Approximately 2% of the transformants were trimethoprim-resistant. Plasmid pPL608-TR1 is the plasmid from one such clone. Mammalian DHFR is resistant to the drug trimethoprim (Tp) whereas the bacterial enzyme is sensitive.

Strain BGSCIS53 harboring pPL608-TR1 grew as small colonies on MinCH-Tp but produced large colonies on drug-free media, suggesting that the amount of mouse DHFR synthesized in IS53 was insufficient to permit completely normal growth in the presence of Tp. Spontaneous variants exhibiting enhanced expression of DHFR were identified as rare large colonies on MinCH-Tp. The large colony phenotype cotransformed with plasmid isolated from one such variant, indicating the variant phenotype resulted from a change in the plasmid. This mutant plasmid was designated pPL623-TR1. Plasmids pPL608-TR1 and pPL623-TR1 exhibit the same copy number in BGSCIS53, approximately 40–50, and both plasmids exhibit the same DNA fragment pattern after digestion with EcoRI, HaeIII, PstI, HpaII, HindIII or BglII restriction enzymes. The mutation which produced the plasmid of the invention was such that one additional nucleotide (adenosine) was inserted in the EcoRI to PstI fragment downstream from the promoter. The nucleotide sequence for the promoter and this fragment is given in FIG. 1.

Materials and Methods

Unless otherwise specified, percentages used in this section are by weight per unit volume.

Bacteria and Media

*Bacillus subtilis* strain BGSCIS53 was used in all experiments. Penassay broth was from Difco. MinCH-Tp is MinCH containing 25 μg/ml of Tp. MinCH medium has been described by Spizizen, Proc. Natl. Acad. Sci. U.S.A. 44, 1072–1078 (1958).

Enzyme Assays

CAT was assayed by the procedure described by Shaw [Shaw, Methods Enzymol. 43, 737–755 (1975)]. DHFR was assayed by the method of Hanggi and Littlefield, J. Biol., Chem. 249, 1390–1397 (1974). The Bradford method was used to determine protein concentration [Bradford, Anal. Biochem. 72, 248–254 (1976)].

Plasmid Manipulations

Plasmid purification, agarose gel electrophoresis and transformation of *B. subtilis* were performed using methods quite similar to those described by Lovett and Keggins, Methods Enzymol. 68, 342–357 (1979). Restriction enzymes and DNA ligase were from New England Biolabs and were used pursuant to supplier's instructions.

RNA Isolation

*B. subtilis* cells harboring a plasmid of the invention were grown in 500 ml of penassay broth and harvested at mid-exponential growth by centrifugation at 16,000×g for 10 minutes. The resulting cell pellet was resuspended in 50 ml of protoplast solution (2×penassay broth, 0.5M sucrose, 0.2M maleate, 0.2M MgCl$_2$ and 0.2 mg/ml lysozyme) and incubated at 37° C. with gentle shaking until protoplast formed, i.e., about 30 minutes. The protoplasts were harvested by centrifugation at 3000×g for 10 minutes and resuspended in 10 ml of boiling lysis solution, i.e., 0.1M NaCl, 0.5% sodium dodecyl sulfate (SDS), and 0.01M ethylenediaminetetraacetic acid (EDTA), see Young and Furano, Cell 24, 695–706 (1981). All glassware used subsequent to this step was acid washed. After cooling the lysis solution to 37° C., proteinase K (50 μg/ml) was added. The resulting suspension was incubated at 37° C. for 1 hr and then the RNA was denatured by extraction with phenol three times. Ethanol, 2.5 volumes per volume of extract, was added to precipitate the RNA as a pellet which was then dried. The resulting dried pellet was resuspended in 10 ml of DNase buffer (10 mM sodium acetate, pH 5.0, 50 mM NaCl and 1 mM MnCl$_2$) containing 30 μg/ml DNase I (Worthington, RNase-free) and the resulting suspension was incubated for 30 minutes at 37° C. Next, 0.5 ml of 10% SDS, 0.2 ml of 0.5 M EDTA and sufficient proteinase K to give a concentration of 50 μg/ml were added. Incubation at 37° C. was continued for a total time of one hour. The RNA was denatured by extraction three times with phenol and was precipitated by adding to the extract ethanol in proportions as described above. The resulting dried RNA pellet was resuspended in a desired buffer. This procedure was utilized to show that the promoter fragment was operating as a promoter to turn the DHFR gene on so as to produce RNA complementary to the DHFR gene.

RNA Electrophoresis, Transfer to Chemically Activated Paper and Hybridization

RNA was denatured in 1M glyoxal, 10 mM sodium phosphate, pH 7.0 for 60 minutes at 50° C.; see McMaster and Carmichael, Proc. Natl. Acad. Sci. U.S.A. 74, 4835–4838 (1977). The resulting denatured RNA was loaded onto 1.5% agarose gel made with 10 mM sodium phosphate, pH 7.0. Electrophoresis with this gel was run at 75 ma for 3 hours. Thereafter, the gel was stained in 30 μg/ml acridine orange to effect visualization of the RNA for photography using an ultraviolet light source. The RNA was transferred to diazobenzyloxymethyl (DBM) paper using a procedure similar to that described by Smith and Summers, Anal. Biochem 109, 123–129 (1980). The DBM paper was prepared from aminobenzyloxymethyl paper according to the procedure of the manufacturer Bio-Rad. DNA was nick translated and hybridized to the RNA according to the methods of Alwine et al., Methods Enzymol. 68, 220–242 (1979); and Schoner and Littlefield, Nuc. Acids Res. 9, 6601–6613, (1981).

DNA Sequencing

DNA sequencing was conducted by the method of Sanger et al., Proc. Natl. Acad. Sci. U.S.A. 74, 5463–5467 (1977).

The invention is further illustrated by the following examples. Molecular weights given herein are approximate and are based upon comparisons with fragments of known molecular weight.

EXAMPLE 1

Expression of Mouse DHFR in Plasmid pPL632-TR1

The activity of mouse DHFR is inhibited by methotrexate in a stoichiometric relationship, Werkheiser, J. Biol. Chem. 236, 888–893 (1961). Titration of mouse DHFR activity with known concentrations of methotrexate provides an estimate of the number of mouse DHFR molecules present.

Extracts prepared from strain BGSCIS53 harboring individually pPL608-TR1 and pPL623-TR1 were incubated with varying concentrations of methotrexate to determine the drug concentration inhibiting 50% of the DHFR activity. Results are depicted in the FIG. 2. After correcting for differences in the protein concentration of the two extracts, the DHFR concentration in extracts of cells harboring pPL623-TR1 was $1.67 \times 10^{-8}$M, whereas the concentration of the pPL608-TR1 specified enzyme was $0.82 \times 10^{-9}$M. The molecular weight of mouse DHFR is 21,500 daltons. By assuming 80,000 molecules are equivalent to 1% of the total cell protein, it was calculated that 0.2% of the cell protein in BGSCIS53-pPL623-TR1 was mouse DHFR.

To determine if the mouse DHFR produced in B. subtilis was comparable to the native mouse enzyme, trimethoprim-insensitive DHFR activity was purified approximately 280-fold from extracts of exponentially growing strain BGSCIS53 having plasmid pPL623-TR1 transformed into it. This purification enriched for a protein that precisely comigrated with natural mouse DHFR in sodium dodecyl sulfate-PAG electrophoresis, suggesting that the DHFR produced was identical to natural mouse DHFR.

Comparison of the specific activities of mouse DHFR and chloramphenicol acetyl transferase in extracts prepared by B. subtilis strain BGSCIS53 cells harboring plasmid pPL608-TR1 or pPL623-TR1 demonstrated that the mutation which exists in the latter plasmid enhanced the specific activity of mouse DHFR approximately 12-fold. However, the specific activity of CAT, which is controlled by the same promoter fragment but is coded for by a gene proximal to the DHFR gene end distal with respect to the promoter, was not altered by the mutation. Results are presented in the Table 1.

TABLE 1

| Plasmid in IS53 | Presence or absence of Cm in growth media | Specific DHFR[b] | activity[a] CAT[c] |
|---|---|---|---|
| pPL608-TR1 | − | 0.10 | 0.61 |
| pPL608-TR1 | + | 0.12 | 4.14 |
| pPL623-TR1 | − | 1.79 | 0.53 |
| pPL623-TR1 | + | 0.92 | 4.51 |

[a]Cells were grown in penassay broth to mid-log phase in the presence (+) or absence (−) of 5 μg/ml of chloramphenicol (Cm).
[b]nmoles of folate reduced/min/mg protein at 37° C.
[c]mmoles of Cm acetylated/min/mg protein at 25° C.

EXAMPLE 2

Expression of Human Interferon

The DHFR gene was removed from plasmid pPL623-TR1 by digestion with PstI and ligation with T4 ligase to give a plasmid labeled pPL623. B. subtilis strain BGSCIS53 transformed with pPL623 has been deposited with ATCC and bears deposit accession number ATCC 39294. A Tn9 CAT gene was inserted at the PstI site of pPL623. The resulting plasmid and a β-interferon E. coli plasmid were cleaved with HindIII and joined and ligated with T4 DNA ligase. Of the resulting two possible orientations, a plasmid was selected with an orientation in which the functional direction of the promoter was in the same direction as the interferon gene. A fragment between the BglII site of the β-interferon (IFN) gene and the BglII site in the pPL623 plasmid was cleaved and replaced with a BamHI/BglII fragment from plasmid pUB110 producing plasmid pSA3. Plasmid pSA3 was digested with BglI and XbaI restriction enzymes, gap-filled with DNA polymerase I, [see Methods Enzymol. 68 (1979)], annealed and ligated to give an interferon gene containing plasmid labeled pSA3-1.

Plasmid pSA3 was digested with BglI and then HindIII, gap-filled with DNA polymerase I, annealed and ligated to give a plasmid designated pSA3-12. Transformed B. subtilis strain BGSCIS53 harboring pSA3-12 has been deposited with ATCC and bears deposit accession number ATCC 39292. Plasmid pSA3-12 has a molecular weight of about 4.56 Md. Plasmid pSA3-12 was cleaved with restriction enzymes XbaI and BclI. The resulting DNA was gap-filled and then blunt-end ligation was performed on the resulting material to provide a plasmid designated pSA XΔB and having a molecular weight of about 4.56 Md. Transformed *B. subtilis* strain BGSCIS53 harboring pSA XΔB has been deposited with ATCC and bears deposit accession number ATCC 39293. Plasmid pSA3-1 was also digested completely with enzyme PstI thereby removing about one-third of the interferon gene and the Tn9 gene from the plasmid. The resulting plasmid was designated pSA PstΔ and was used as a control because it was expected to give no interferon activity.

Figure 3:
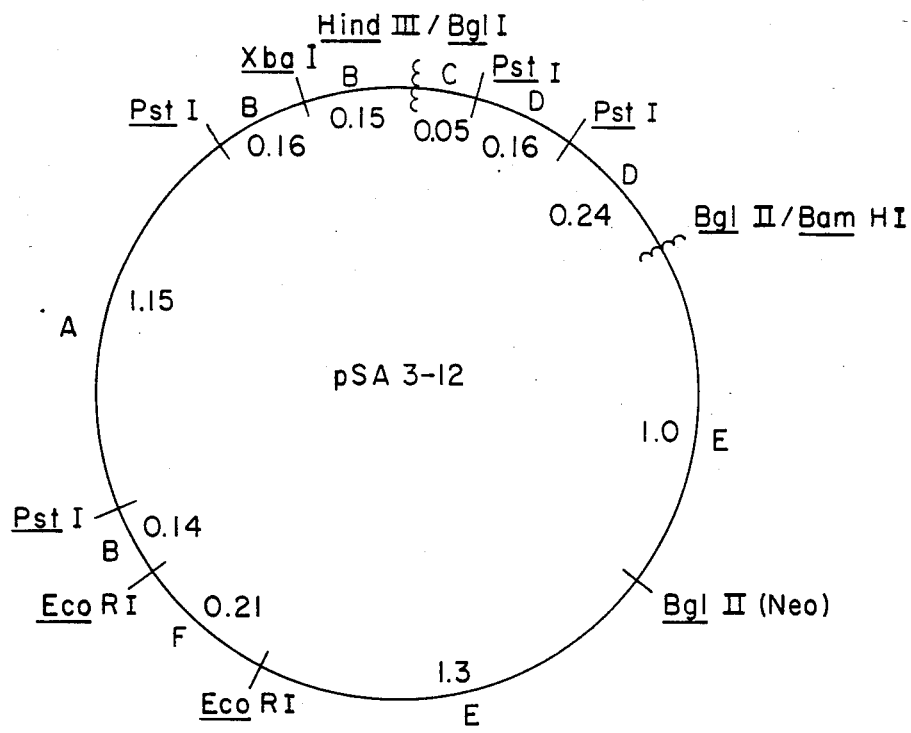
FIGS. 3 and 4 are endonuclease restriction maps for plasmids of the invention.
Figure 4:
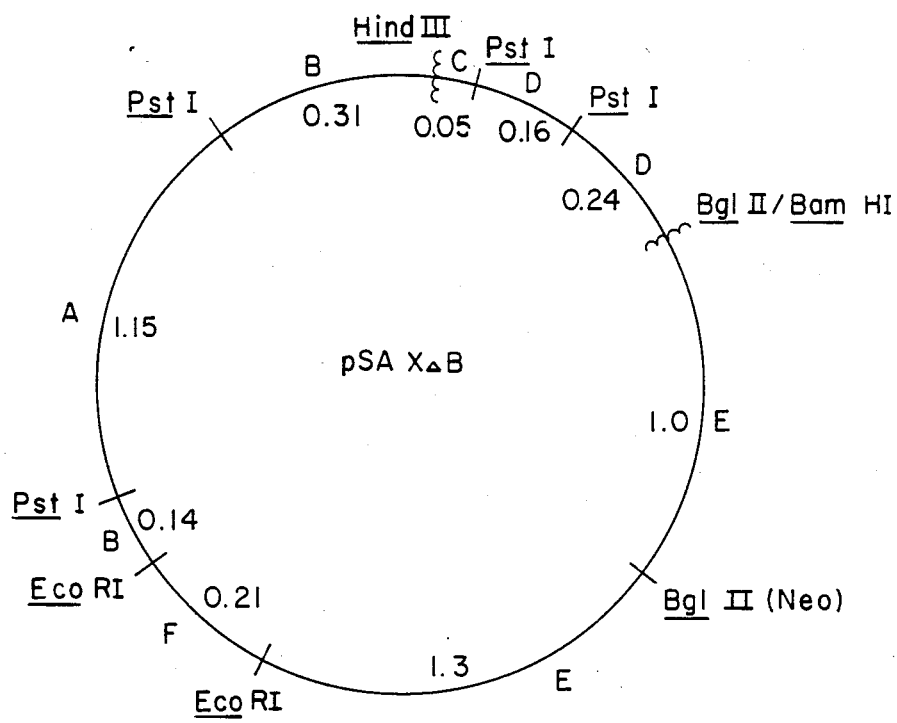

Four of the foregoing plasmids were used to transform *B. subtilis* strain BGSCIS53 and the resulting transformed cells were assayed for interferon activity according to the method of Knight and Fahey, J. Interferon Res. 2, p 422 (1982). The results are presented in Table 2. Restriction endonuclease cleavage maps for pSA3-12 and pSA XΔB are presented in FIGS. 3 and 4, respectively. The numbers around the perimeter of each map are the approximate molecular weights of the respective fragments and the letters are defined in the figures and denote the source of each fragment.

Table 2 shows that for plasmid pSA3-12 interferon activity was obtained about 33% of the time whereas for plasmid pSA3-1 no activity was detected. Lack of detection of interferon activity for PSA3-1 does not prove conclusively that interferon was not expressed since other factors, such as instability of the interferon produced and degradation of the interferon by the cells, could cause the same result. For pSA XΔB low interferon activity was detected in one out of four assays.

The work described herein was all done in conformity with physical and biological containment requirements specified in the NIH guidelines.

TABLE 2

| INTERFERON ACTIVITY | |
|---|---|
| Plasmids | β-Interferon Activity Units/liter |
| pSA3-1 (cells) | <5 |
| pSA3-1 | <5 |
| pSA3-1 (medium) | <5 |
| pSA3-12 | 7600 |
| pSA3-12 | 320 |
| pSA3-12 (cells) | <5 |
| pSA3-12 (medium) | <5 |

TABLE 2-continued

| INTERFERON ACTIVITY | |
|---|---|
| Plasmids | β-Interferon Activity Units/liter |
| pSA3-12 | <5 |
| pSA3-12 | <5 |
| pSA XΔB | 80 |
| pSA XΔB | <5 |
| pSA XΔB (cell protein) | <5 |
| pSA XΔB (medium) | <5 |
| pSA PstΔ (cells) | <5 |
| pSA PstΔ (medium) | <5 |

What is claimed is:

1. A plasmid useful for introducing into *B. subtilis* foreign DNA, the nucleic acid sequence of which codes for production of a desired product, said plasmid being characterized as follows:
   (a) it is comprised of (1) a double-stranded DNA segment of *B. pumilus* strain NCIB8600 containing a chloramphenicol acetyltransferase gene plus an EcoRI* promoter fragment cloned from phage SPO2 DNA and (2) a portion of a *B. subtilis* plasmid pUB110; and
   (b) it has a mutation in its EcoRI to PstI fragment downstream from the promoter fragment whereby the nucleotide sequence for this EcoRI to PstI fragment is that shown in FIG. 1 of the drawing.

2. A plasmid according to claim 1 wherein the foreign DNA codes for the production of human interferon.

3. A plasmid according to claim 2 wherein the human interferon is β-interferon.

4. A plasmid according to claim 1 wherein the *B. pumilus* segment is about 0.8 Md in molecular weight and the promoter fragment has a molecular weight of about 0.2 Md.

5. A plasmid according to claim 4 wherein the plasmid has a molecular weight of about 3.3 Md.

6. A plasmid according to claim 4 wherein the foreign DNA is a mouse gene coding for dihydrofolate reductase.

7. Plasmid pSA3-12 characterized as shown by endonuclease restriction map of FIG. 3 of the drawing and having a molecular weight of about 4.56 Md.

8. Plasmid pSA-XΔB characterized as shown by endonuclease restriction map of FIG. 4 of the drawing and having a molecular weight of about 4.56 Md.

9. *B. subtilis* strain BGSCIS53 (pPL623), having the deposit accession number ATCC 39294.

10. *B. subtilis* strain BGSCIS53 (pSA3-12), having the deposit accession number ATCC 39292.

11. *B. subtilis* strain BGSCIS53 (pSA XΔB), having the deposit accession number ATCC 39293.

* * * * *